(12) United States Patent
Scherz et al.

(10) Patent No.: US 6,333,319 B1
(45) Date of Patent: Dec. 25, 2001

(54) SYNTHETIC METAL-SUBSTITUTED BACTERIOCHLOROPHYLL DERIVATIVES AND USE THEREOF

(75) Inventors: Avigdor Scherz; Yoram Salomon, both of Rehovot (IL); Hugo Scheer, Blonhofer; Gerhard Hartwich, Munich, both of (DE); Alexander Brandis, Rehovot (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 09/077,208

(22) PCT Filed: Nov. 24, 1996

(86) PCT No.: PCT/IL96/00161

§ 371 Date: Nov. 13, 1998

§ 102(e) Date: Nov. 13, 1998

(87) PCT Pub. No.: WO97/19081

PCT Pub. Date: May 29, 1997

(30) Foreign Application Priority Data

Nov. 24, 1995 (IL) .......................................... 116126

(51) Int. Cl.⁷ ....................... A61K 31/555; C07D 487/22
(52) U.S. Cl. ............................. 514/185; 540/145
(58) Field of Search .............................. 514/185; 540/145

(56) References Cited

FOREIGN PATENT DOCUMENTS

| 41 21 876 | 1/1993 | (DE) . |
|---|---|---|
| 0 584 552 | 3/1994 | (EP) . |
| 584552 A2 | * 3/1994 | (EP) . |
| 90/12573 | * 11/1990 | (WO) . |
| 95/32206 | * 11/1995 | (WO) . |

OTHER PUBLICATIONS

DeJordy et al, "Correlation of MR imaging and Histologic Findings in Mouse Melanoma", *J. Magn. Reson. Imag.* 2:695–700 (1992).

Donohoe et al, "Resonance Raman spectra and normal mode descriptions of a bacteriochlorophyll of a model complex", *Chemical Abstracts* 110(9):381 Abstract No. 72667k (1989).

Gerst et al, "Regulation of adenylate cyclase by β–melanotropin in the M2R melanoma cell line", *Mol. Cell. Endocrinol.* 46:137–147 (1986).

Geskes et al, "An Electrochemical and Spectroelectrochemical Investigation of Metal–Substituted Bacteriochlorophyl a", *J. Am.Chem.Soc.* 117(29):7776–7783 (1995).

Omata et al, "Preparation of Chlorophyll a, Chlorophyll b and Bacteriochlorophyll a by Column Chromatography with DEAE–Sepharose CL–6B and Sepharose CL–6B", *Plant & Cell Physiol.* 24(6):1093–1100 (1983).

Schaber et al, "High–Performance Liquid Chromatographic Study of the Chlorophyll Allomerization Reaction", *J. Chromatogr.* 316:25–41 (1984).

Strell et al, "New Methods for Introduction of Meals into Derivatives of Chlorophyll", *Liebigs Ann. Chem..* pp. 970–974 (1977).

Tamiaki et al, "Self–Assembly of an Artificial Light–Harvesting Antenna: Energy Transfer from a Zinc Chlorin to a Bacgteriochlorin in a Supramolecular Aggregate", *Angew. Chem. Int. Ed. Engl.* 35(7):772–774 (1996).

* cited by examiner

*Primary Examiner*—T. A. Solola
(74) *Attorney, Agent, or Firm*—Browdy and Neimark

(57) ABSTRACT

The present invention relates to a new method of preparation of metalated bacteriochlorophyll derivatives for use in methods of in vivo photodynamic therapy (PDT) and diagnosis and in vitro photodynamic killing of viruses and microorganisms, and to some novel metal-substituted bacteriochlorophyll derivatives.

17 Claims, 1 Drawing Sheet

SYNTHETIC METAL-SUBSTITUTED BACTERIOCHLOROPHYLL DERIVATIVES AND USE THEREOF

This appln. is a 371 of PCT/IL 96/00161 filed Nov. 24, 1996.

FIELD OF THE INVENTION

The present invention relates to a new method of preparation of metalated bacteriochlorophyll derivatives for use in methods of in vivo photodynamic therapy (PDT) and diagnosis and in vitro photodynamic killing of viruses and microorganisms, and to some novel metal-substituted bacteriochiorophyll derivatives.

DEFINITIONS AND ABBREVIATIONS

BChl=bacteriochlorophyll a (the Mg-containing 7,8,17,18-tetrahydroporphyrin of the formula I hereinafter wherein M is Mg, $R_1$ is phytyl or geranylgeranyl, $R_2$ is $COOCH_3$, $R_3$ is H, $R_4$ at position 3 is acetyl and at position 8 is ethyl).

BChl derivative=a derivative of BChl with modifications in the macrocycle, the central metal atom and/or in the periphery, including the derivatives of formulas I, II, III and I', II', III' hereinafter.

BPhe=bacteriopheophytin a (BChl in which the central Mg is replaced by two H atoms).

Chl=chlorophyll (a Mg-containing 17,18-dihydroporphyrin derivative made of a macrocycle consisting of 4 pyrrole and one isocychlic ring that are conjugated to each other and linked to the atom of Mg). Chlorophyll a has the formula I hereinafter wherein $R_1$ is phytyl. $R_2$ is $COOCH_3$, $R_3$ is H, $R_4$ at position 3 is vinyl and at position 8 is ethyl.

[M]-BChl=BChl derivative in which the central Mg atom has been replaced by a metal M as defined hereinafer.

PDT=photodynamic therapy

Phe=pheophytin a (Chl in which the central Mg is replaced by two H atoms).

BACKGROUND OF THE INVENTION

The Mg-containing (bacterio)chlorophylls ((B)Chl) and their free bases, the (bacterio)pheophytins ((B)Phe), are essential to photosynthesis. They act as antenna or redox pigments enabling light-induced charge separation within the reaction center. The pigments are also potentially useful photosensitizers, e.g. in photodynamic tumor therapy.

Porphyrins have been shown to accumulate in tumor tissue and, upon irradiation of the tumor tissue, to absorb light in situ, providing a mean to detect tumors by location of the fluorescence. A crude derivative of hematoporphyrin, known as hematoporphyrin derivative or HPD, has been proposed both for detection and for photodynamic therapy of tumors. A form of HPD said to be more effective comprises a portion of HPD having an aggregate weight over 10 Kda and is the subject of U.S. Pat. No. 4,649,151. HPD or its active components have been described in U.S. Pat. No. 4,753,958 for topical treatment of skin diseases, and in Matthews et al., 1988, for sterilization of biological samples containing infectious organisms such as bacteria and virus.

In order to optimize the performance of the porphyrin drugs in therapeutics and diagnostics, several porphyrin derivatives have been proposed in which, for example, there is a central metal atom complexed to the four pyrrole rings, and/or the peripheral substituents of the pyrrole rings are modified and/or the macrocycle is dihydrogenated to Chl derivatives (chlorins) or tetrahydrogenated to BChl derivatives (bacteriochlorins).

Complexes of cyclic tetrapyrroles with metals other than Mg were studied in the porphyrin and 17,18-dihydroporphyrin series to understand their spectrocospic and redox properties (Hynninen, 1991). Bacteriochlorophylls are of potential advantage compared to the chlorophylls because they show intense near-infrared bands, i.e. at considerably longer wavelengths than chlorophyll derivatives. However, little information is presently available on bacteriochlorophylls with central metals other than Mg.

PCT International Application Publication No. WO 90/12573 to Dougherty describes derivatives of bacteriochlorophyll-a or -b or of the corresponding bacteriochlorins devoid of the central metal atom or in which the central metal atom may be a non-paramagnetic metal selected from $Mg^{2+}$, $Sn^{2+}$ and $Zn^{2+}$, and the C-$17^3$-carboxyl group is esterified with a saturated or unsaturated hydrocarbyl residue of 8–25C, for the manufacture of a composition for use in a method to effect the destruction or impairment of undesired target biological substrates, which method comprises photosensitizing said substrate with an effective amount of said derivative, followed by irradiation of the target substrate with radiation in a wavelength band absorbed by said derivative for a time effective to impair or destroy the substrate. In addition, the compounds are said to be useful in photodynamic therapy and diagnostics. It is to be noted that although $Sn^{2+}$ and $Zn^{2+}$ complexes of bacteriochlorophyll-a or -b are claimed, these metal derivatives have not been exemplified nor was any method for their preparation described in the specification of said patent application WO 90/12573.

Losev et al, 1990, describe [Pd]—BChl and [Cu]—BChl complexes said to be prepared by direct metalation of BPhe with Pd benzonitrile in benzene in a stream of nitrogen or with a concentrated solution of $CuCl_2$ in methanol, respectively. However, this publication lacks details of the method of preparation and characterization of the metal complexes. Moreover, the preparation of the [Pd]—BChl complex according to Losev could not be repeated by us.

Under normal delivery conditions, i.e. in the presence of oxygen at room temperature and under normal light conditions, the BChl moieties are labile and have somewhat lower quantum yields for triplet state formation, when compared with, e.g., hematoporphyrin derivative (HPD). However, their possible initiation of biological redox reactions, favorable spectral characteristics and their ready degradation in vivo result in the potential superiority of bacteriochlorophylls over other compounds, e.g. porphyrins and chlorophylls, for PDT therapy and diagnostics and for killing of cells, viruses and bacteria in samples and in living tissue. Chemical modification of bacteriochlorophylls is expected to further improve their properties, but this has been very limited due to lack of suitable methods for the preparation of such modified bacteriochlorophylls (Hynninen, 1991).

European Patent Application published under No. 0584552 of the same applicant of the present application describes new conjugates of Chl and BChl with amino acids, peptides and proteins for use in PDT therapy and diagnostics. The amino acid, peptide or protein residue is linked directly or via a spacer to the C-$17^3$-carboxyl group of the Chl or BChl molecule. These conjugates are prepared by methods which are mild enough to retain the acid-labile central Mg atom. Zn and Cu complexes of chlorophyll a-17³-serine methyl ester were also described therein, but no metalated bacteriochlorophyll nor a method for their preparation was described therein.

German Patent Application No. DE 4121876 describes bacteriochlorophyll derivatives in which modified esters at positions C-13² and C-17³ are obtained under mild conditions by rapid alkaline transesterification, allowing further changes at the isocyclic ring while retaining the central Mg, by which the pigment absorption is shifted beyond 800 nm. The application also mentions metal complexes of said Bchl derivatives with Zn or Ni, but said complexes were not exemplified nor a method for their preparation was described therein.

It would be desirable to prepare new metalated complexes of BChl for use in PDT, in order to maintain or even improve the favorable optical and physiological properties of BChls while optimizing their photosensitizing potential as well as improving their chemical stability and optimizing their physiological lifetimes. Transmetalation results in distinct changes in the chemical reactivity and stability of the BChls, which are important for new modifications of the macrocycle and the peripheral substituents, and in particular for optimizing their transport, targeting and biological lifetime and minimizing toxic side effects. Transmetalation also results in distinct changes in the excited state properties, including triplet yield and lifetime, accessibility of higher excited states, and production of cytotoxic oxygen species.

Several methods are known for variation of the central metal atom in porphyrins (see Buchler, 1975). Porphyrins are readily accessible and chemically stable, yet spectrally and physiologically unfavorable.

Few methods are known for direct or indirect metalation of chlorophylls. Strell and Urumow, 1977, describe [Cr]—Chl and [Mn]—Chl complexes prepared by transmetalation of the [Cd]—Chl complex (obtained by reaction of the demetalated Chl derivative with cadmium acetate in methanol or pyridine) with the acetate of $Cr^{++}$ or Mn in methanol under $N_2$ atmosphere. This transmetalation method is said to be suitable also for Cu, Zn, Co and Pb complexes of chlorophyll derivatives, but not for $Fe^{3+}$, Ni and Mg. However, since the Cu, Zn, Co and Pb complexes can be prepared by direct metalation into Phe, the method would be advantageous only for Cr and Mn. The authors also describe preparation of the [Mg]—Chl complex by direct metalation of Phe in acetone with Mg acetate in dimethylsulfoxide.

Little information is presently available on bacteriochlorophylls with central metals other than Mg. Metalation of bacteriochlorophylls is known to be more difficult than that of chlorophylls due to their decreased reactivity for metalation and increased reactivity for side reactions. A specific method for insertion of Mg into bacteriopheophytin a has been described (Wasielewsky, 1977). The present inventors have tried the direct metalation and transmetalation procedures for chlorophyll derivatives described by Strell and Urumow for the preparation of metal complexes of bacteriochlorophyll derivatives, but all attempts were unsuccessful. The direct metalation of bacteriopheophytin derivatives did not work with any metal tried, except for Cu and Zn, and resulted otherwise in a mixture of unreacted bacteriopheophytin and metalated oxidation products of the 3-acetylchlorophyll a type.

SUMMARY OF THE INVENTION

It has now been found in accordance with the present invention that metal complexes of bacteriochlorophyll derivatives can be obtained by a modification of the transmetalation process for metalation of chlorophyll derivatives published by Strell and Urumow, by using appropriate metal salts and solvents.

The present invention thus relates to a new process for the preparation of synthetic metalated bacteriochlorophyll derivatives of the formula:

wherein

BChl represents the residue of a demetalated natural or synthetic bacteriochlorophyll derivative carrying at position 17³ a group —$COOR_1$ wherein $R_1$ is a $C_1$–$C_{25}$ hydrocarbyl residue, and M represents a metal with an ionic radius smaller than that of Cd (r≅95 pm), said metal M being selected from the group consisting of a divalent metal selected from the group consisting of Pd, Co, Ni, Cu, Zn and Mn, a trivalent metal selected from the group consisting of Fe, Mn and Cr, and a tetravalent metal selected from the group comprising Sn and Pt, which process comprises:

(i) reacting an appropriate bacteriopheophytin derivative carrying at position 17³ a group —COOR, as defined above, dissolved in dimethyl formamide with dehydrated Cd acetate in Ar atmosphere and recovering the [Cd]—BChl complex from the reaction mixture by chromatography under reducing conditions;

(ii) dissolving the thus produced [Cd]—BChl complex dissolved in dry acetone with an appropriate dehydrated metal M salt selected from metal M chloride, acetate and acetyl-acetonate in Ar atmosphere; and (iii) recovering the desired metalated [M]—BChl derivative from the reaction mixture.

In one embodiment, the process of the invention is applied to the preparation of metalated BChl derivatives of the formula I, II or III:

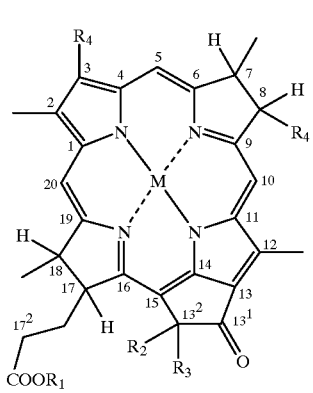

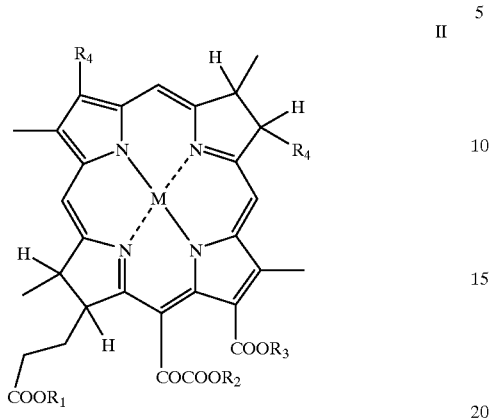

II

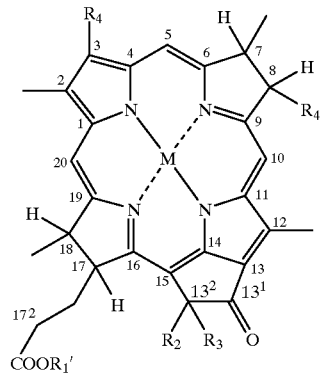

I'

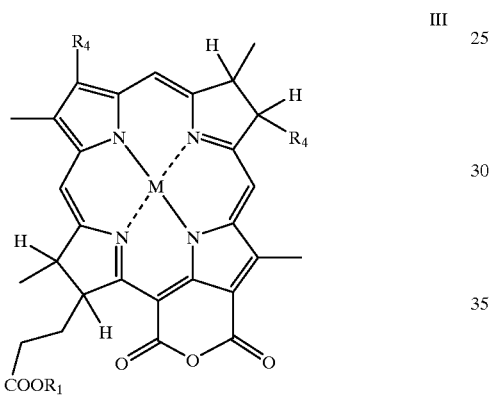

III

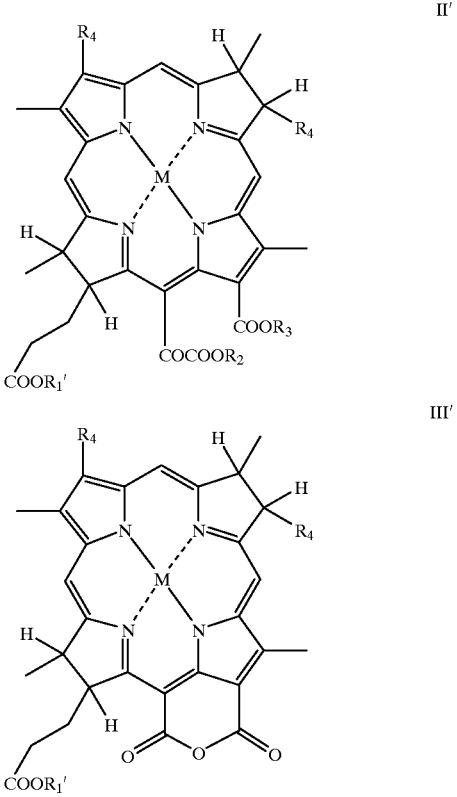

II'

III' wherein

R'₁ is a $C_1$–$C_{25}$ hydrocarbyl residue;

$R_2$ is H, OH or: $COOR_5$, wherein R5 is $C_1$–$C_{12}$ alkyl or $C_3$–$C_{12}$ cycloalkyl;

$R_3$ is H, OH or $C_1$–$C_{12}$ alkyl or alkoxy;

$R_4$ is each independently selected from the group consisting of vinyl, ethyl, acetyl, 1-hydroxyethyl and ethers and esters thereof; and M represents a metal with an ionic radius smaller than that of Cd (r≅95 pm), said metal M being selected from the group consisting of a divalent metal selected from the group consisting of Pd, Co, Ni, Cu, Zn and Mn, a trivalent metal selected from the group consisting of Fe, Mn and Cr, and a tetravalent metal selected from the group comprising Sn and Pt.

From the above [MN]—BChl derivatives of formulas I, II and III further derivatives can be obtained by transesterification at position $17^3$ and thus, in another aspect, the invention relates to a process for the preparation of compounds of the formulas I', II' and III':

wherein

R', is selected from the group consisting of:
(i) a $C_1$–$C_{25}$ hydrocarbyl residue optionally substituted by halogen, oxo (=O), OH, CHO, COOH, or $NH_2$, or such a residue interrupted by one or more heteroatoms selected from O, S and NH, or by a phenyl ring;
(ii) a residue of an amino acid or of a peptide containing a hydroxy group or a derivative thereof selected from the group consisting of esters and N-protected derivatives, wherein said hydroxylated amino acid or derivative thereof is linked to the COO— residue through the hydroxy group;

(iii) a residue of a peptide as defined in (ii) linked to the COO— residue via a spacer as defined in (i) wherein said $C_1$–$C_{25}$ saturated or unsaturated hydrocarbyl residue optionally substituted by halogen, oxo, OH, CHO, COOH, or $NH_2$, or such a residue interrupted by one or more heteroatoms selected from O, S and NH, or by a phenyl ring, is further substituted by an end functional group selected from OH, COOH, or $NH_2$; and (iv) a residue of a cell-specific ligand selected from a peptide and a protein directly linked to the COO— residue or via a spacer as defined in (i) wherein said $C_1$–$C_{25}$ saturated or unsaturated hydrocarbyl residue optionally substituted by halogen, oxo, OH, CHO, COOH, or $NH_2$, or interrupted by one or more heteroatoms selected from O, S and NH, or by a phenyl ring, is further substituted by an end functional group selected from OH, COOH, or $NH_2$;

$R_2$ is H, OH or $COOR_5$, wherein $R_5$ is $C_1$–$C_{12}$ alkyl or $C_3$–$C_{12}$ cycloalkyl;

$R_3$ is H, OH or $C_1$–$C_{12}$ alkyl or alkoxy;

$R_4$ is each independently selected from the group consisting of vinyl, ethyl, acetyl, 1-hydroxyethyl and ethers and esters thereof; and M represents a metal with an ionic radius smaller than that of Cd (r≅95 pm), said metal M being selected from the group consisting of a divalent metal selected from the group consisting of Pd, Co, Ni, Cu, Zn and Mn, a trivalent metal selected from the group consisting of Fe, Mn and Cr, and a tetravalent metal selected from the group comprising Sn and Pt, which process comprises:

(i) reacting an appropriate bacteriopheophytin derived from a bacteriochlorophyll derivative of formula I, II or III carrying at position $17^3$ a group —$COOR_1$ wherein $R_1$ is a $C_1$–$C_{25}$ hydrocarbyl residue, dissolved in dimethyl formamide, with dehydrated Cd acetate in Ar atmosphere, and recovering the corresponding [Cd]—BChl complex from the reaction mixture by chromatography under reducing conditions;

(ii) reacting the thus produced [Cd]—BChl complex dissolved in dry acetone with an appropriate dehydrated metal M salt selected from metal M chloride, acetate and acetyl-acetonate in Ar atmosphere; and (iii) reacting the produced metalated [M]—BChl derivative recovered from the reaction mixture with a compound of the formula $R'_1$—OH, under transesterification conditions, to obtain a compound of formula I', II' or III' wherein $R'_1$ is as defined above.

In a preferred embodiment, the [M]—BChl derivative is a [M]—BChl derivative wherein $R_1$ is phytyl or geranylgeranyl, $R_2$ is $COOCH_3$, $R_3$ is H, $R_4$ at position 3 is acetyl and at position 8 is ethyl and the metal M is Pd, Cu, Ni, Co, Zn and Mn. In another preferred embodiment, the metal M salt employed in step (ii) is a metal chloride.

In another further embodiment, steps (i) and (ii) can be combined into one single step;, i.e. the bacteriopheophytin derivative is reacted with an excess of the appropriate dehydrated metal M salt, e.g. metal chloride, in the presence of catalytic amounts of the dehydrated Cd salt, e.g. Cd acetate, in dimethylformamide or acetone.

In another aspect, the present invention relates to new metalated bacteriochlorophyll derivatives of the formulas I', II' and III' as defined above, but excluding the compounds of formula I wherein $R_2$ is $COOCH_3$, $R_3$ is H, $R_4$ at position 3 is acetyl and at position 8 is ethyl, and $R_1$ is phytyl or ethyl and M is Pd or $R_1$ is phytyl and M is Cu.

The new metalobacteriochlorophyll derivatives of the invention of formulas I', II' and III' as defined above are for use as photosensitizers as therapeutic and diagnostic agents, and for killing cells, viruses and bacteria in samples and living tissues, as well known in the art for HPD and other photosensitizers.

DETAILED DESCRIPTION OF THE INVENTION

Figure 1:
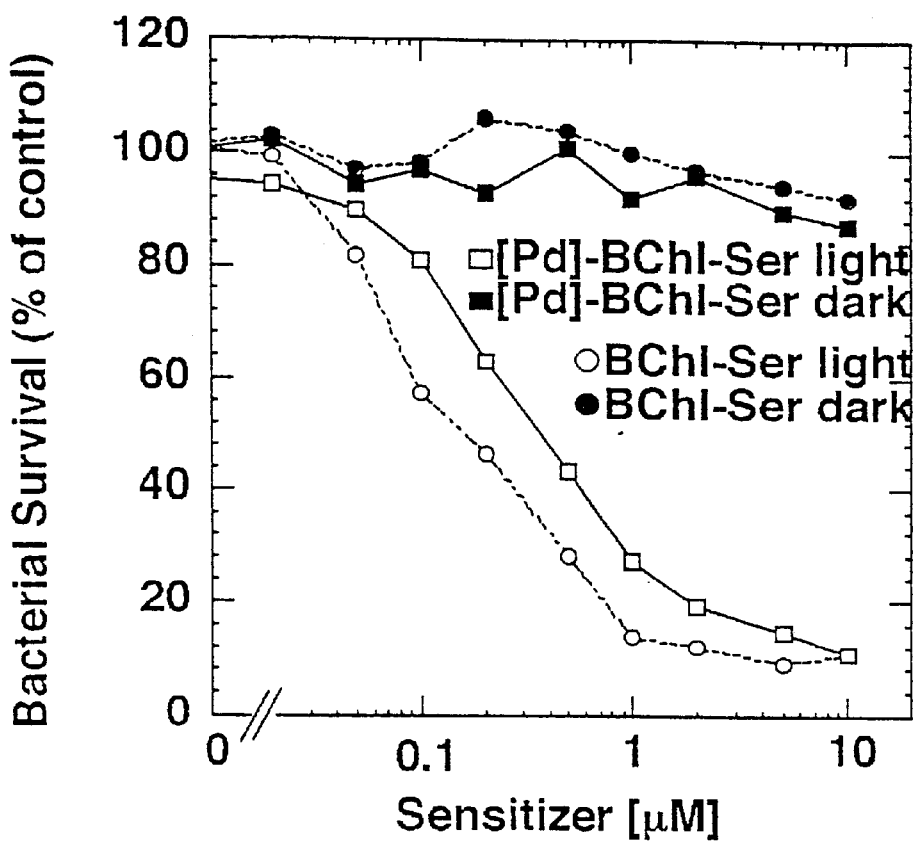
FIG. 1 shows the phototoxicity of [Pd]—BChl—$17^3$-seryl methyl ester ([Pd]—BChl-Ser) and BChl-$17^3$-seryl methyl ester (BChl-Ser) on bacterial suspensions of *S. aureus*.

In contrast to porphyrins and chlorophylls, the direct metalation of bacteriochlorophylls is difficult. The method of the present invention allows the obtention of metalated bacteriochlorophyll derivatives having improved properties for use as photosensitizers by transmetalation of the corresponding [Cd]—BChl derivatives.

According to the present invention, [Cd]—BChl complexes, that are readily accessible by the acetate/dimethylformamide method, can be transmetalated in excellent yield to the other metal complexes under mild conditions. The easy transmetalation using [Cd]—BChl as precursor is surprising and probably due in part to the large ionic radius ($r_M$) of $Cd^{2+}$ (95 pm) compared to $Mg^{2+}$ ($r_M$=72 pm). A second factor is the solvent (acetone) in combination with the metals' counter ions (chlorides) used for the reaction. During transmetalation, $CdCl_2$ and [M]—BChl are formed in equilibrium with the educts, and the very low solubility of $CdCl_2$ in acetone shifts the equilibrium to the side of the products.

In one embodiment of the present invention, $R_1$ is any straight or branched, saturated or unsaturated, including aromatic, hydrocarbyl radical, preferably of 1–25 carbon atoms, such as alkyl, alkenyl, phenyl, preferably a lower alkyl of $C_1$–$C_4$ atoms, most preferably ethyl, or a radical derived from natural Bchl compounds, e.g. geranylgeranyl (2,6-dimethyl-2,6-octadienyl) or phytyl(2,6,10,14-tetramethylhexadec-14-en-16-yl); and $R'_1$ is as defined for $R_1$ or is such a hydrocarbon chain substituted by a halogen atom selected from F, Br, Cl and I, or by OH, oxo, CHO, COOH or $NH_2$, or such an optionally substituted hydrocarbyl chain interrupted by O, S or NH, preferably O, e.g. $R'_1$ is an oligooxyethyleneglycol residue of 4 to 10 carbon atoms, preferably pentaoxyethyleneglycol. When $R'_1$ serves as a spacer for a peptide or protein as defined herein, it will have an end functional group selected from OH, COOH and $NH_2$, through which end functional group the peptide or protein is linked by an ester or amide bond.

In another embodiment, $R'_1$ is the residue of an amino acid or of a peptide containing a hydroxy group, such as serine, threonine and tyrosine, or peptides containing them, or a derivative of said amino acid or peptide selected from esters, e.g. alkyl esters, and N-protected derivatives wherein the N-protecting group is for example tert-butoxy, carbobenzoxy or trityl, and said hydroxylated amino acid or peptide or derivative thereof is linked to the COO— group through the hydroxy group. Examples of such amino acid derivatives are serine methyl ester, N-trityl-serine methyl ester, tyrosine methyl ester, and N-tert-butoxy-tyrosine methyl ester, and an example of such a peptide is N-carbobenzoxy-seryl serine methyl ester, all of them prepared as described in EP 0584552. In a most preferred embodiment, the [M]—BChl derivative is [Pd]—BChl esterified with L-serine methyl ester.

In another embodiment, R'$_1$ is the residue of a cell-specific ligand selected from peptides and proteins, which are exemplified by, but not limited to, hormone peptides, e.g. melanocyte-stimulating hormones (melanotropins), and antibodies, e.g. immunoglobulins and tumor-specific antibodies.

The [M]—BChl derivatives of the invention of the formula I' wherein M is Zn or Cu may be prepared also by direct metalation of the demetalated BChl derivative as described hereinafter in Examples 1 to 4.

Some of the metal complexes of bacteriochlorophylls are very stable and thus may be used for further modifications in the periphery of the tetrapyrrole ring system that involve strong conditions such as the use of acetic acid or of a strong mineral acid like hydrochloric or sulfuric acid. Thus, esters, e.g. optionally substituted alkyl or aryl esters, can be formed by reaction of hydroxy groups, for example at position $3^1$ or $13^2$, with the corresponding aliphatic or aromatic acids, acid chlorides or amino acids, and ethers at the same positions are obtained by reaction with the corresponding aliphatic or aromatic alcohols. Compounds having a hydroxy group at position $3^1$, e.g. 3-hydroxyethyl-BChl derivatives, or at position $13^2$, e.g. $13^2$-OH—BChl derivatives, are available by standard procedures (see Struck et al., 1992, and Hinninen, 1991). In addition, the naturally-occurring phytyl and geranylgeranyl esters at position $17^3$ can be transesterified by acid catalysis to other esters, e.g. to ethyl ester, by reaction with the corresponding alcohol. Other substituents can be introduced into the macrocycle ring by Wittig reaction of natural CO groups, such as 3-acetyl in BChl a, or chemically introduced ones like ketoalcohols esterified to C-$17^3$ as well as by oxidative coupling of OH groups to form ether linkages at C-$13^2$, or by acid catalyzed esterification of OH groups, e.g. at C-$3^1$, C-$13^1$, C-$13^2$, with carboxylic acids.

In an alternative, the modifications in the periphery of the tetrapyrrole ring system is carried out in the natural Mg-containing BChl derivative prior to demetalation.

The BChl derivatives of formulas II and III herein may be obtained from the corresponding naturally occurring BChl derivatives of formula I as described previously (Struck, 1990).

The compounds of the invention wherein R'$_1$ is a residue of an amino acid, a peptide or a protein, e.g. antibody, are prepared after the transmetalation procedure of the present invention, by eryymatic transesterification with the enzyme chlorophyllase or by catalytic condensation of the appropriate bacteriochlorophyllide (the free acid BCh-$17^3$-COOH) with the hydroxylated amino acid, peptide or protein using dicyclohexyl-carbodiimide DCC) and N-hydroxysuccinimide (NHS) or 4-dimethylaminopyridine (DMAP) as described in EP 0584552, or by acid-catalyzed reactions not tolerated by Mg complexes like native BChl.

The new metalobacteriochlorophyll derivatives of the invention are for use as photosensitizers as therapeutic and diagnostic agents, and for killing cells, viruses and bacteria in samples and living tissues, as well known in the art for HPD and other photosensitizers. These compounds are useful, for example, in sensitizing neoplastic cells or other abnormal tissue to destruction by irradiation either in vivo or ex vivo using light of appropriate wavelenght. It is believed that the energy of photoactivation is transferred to endogenous oxygen to convert it to singlet oxygen, which singlet oxygen is considered to be responsible for the cytotoxic effect. In addition, the photoactivated forms of the bacteriochlorophylls fluoresce, which fluorescence can aid in localizing tumors or other sites to which the metalated bacteriochlorophylls are administered.

Examples of indications, known in the art, that can be treated with the new metalo-bacteriochlorophyll derivatives of the invention, include destruction of tumor tissue in solid tumors, dissolution of plaques in blood vessels (see, e.g., U.S. Pat No. 4,512,762),; treatment of topical conditions such as acne, athlete's foot, warts, papilloma, and psoriasis, and treatment of biological products (such as blood for transfusion) for infectious agents.

The metalobacteriochlorophyll derivatives of the present invention are formulated into final pharmaceutical compositions for administration to the patient or applied to an in vitro target using techniques well-known in the art, for example, as summarized in Remington's Pharmaceutical Sciences, Mack Publishin Co., Easton, Penna., latest edition. The compositions can be administered systemically, in particular by injection, or can be used topically.

For diagnosis, the metalobacteriochlorophyll derivatives may be used alone or may be labeled with a radioisotope or other detecting means as known in the art.

The amount of metalobacteriochlorophyll derivative to be administered will be according to the experience accumulated with other porphyrins used in PDT, e.g. and will vary depending on the choice of the derivative used as active ingredient, the condition to be treated, the mode of administration, the age and condition of the patient, and the judgement of the physician.

The wavelenght of irradiating light is preferably chosen to match the maximum absorbance of the metalobacteriochlorophyll photosensitizer. The suitable wavelenght for any of the compounds can readily be determined from its absorption spectrum.

In addition to in vivo use, the metalobacteriochlorophyll derivatives of the invention can be used in the treatment of materials in vitro to kill harmfull viruses or infectious agents, such as harmful bacteria. For example, blood and blood plasma to be used for furture transfusion can be treated with a compound of the invention and irradiated to effect sterilization.

The invention thus further relates to pharmaceutical compositions comprising the metalated bacteriochlorophyll derivatives of formulas I', II' and III' herein for photodynamic therapy and diagnosis of malignancies and for photodynamic killing of cells. bacteria and viruses.

For these purposes. the compositions will be prepared and administered by conventional methods, for example, as described in U.S. Pat. Nos. 4,649,151, 4,753,958, 5,256,840 and 5,238,940, European Patent Application No.0584552 and PCT Application No. WO 90/12573, all of them incorporated herein by reference.

The invention will now be illustrated by the following non-limiting examples.

EXAMPLES

In the Examples and Table 1 the starting compounds and the metal complexes obtained will be identified by the following numbers in bold:

| | |
|---|---|
| 1a - BPhe | 1b - BPhe-$13^2$-OH |
| 2a - [Pd] - BChl | 2b - [Pd] - BChl-$13^2$-OH |
| 3a - [Co] - BChl | 3b - [Co] - BChl-$13^2$-OH |

-continued

| | |
|---|---|
| 4a - [Ni] - BChl | 4b - [Ni] - BChl-13²-OH |
| 5a - [Cu] - BChl | 5b - [Cu] - BChl-13²-OH |
| 6a - [Zn] - BChl | 6b - [Zn] - BChl-13²-OH |
| 7a - BChl | 7b - BChl-13²-OH |
| 8a - [Cd] - BChl | 8b - [Cd] - BChl-13²-OH |
| 9a - [Mn] - BChl | 9b - [Mn] - BChl-13²-OH |

Materials and Methods (i) Isolation of BChL BChl [compound 7a] was isolated from photosynthetic bacteria like *Rhodobacter* (Rb) *sphaeroides* or *Rhodospirillum rubrum* according to Scherz and Parson, 1984, Struck et al., 1992, or Svec, 1991. Purification was done on DEAE-Sepharose according to Omata and Murata, 1983.

(ii) Preparation of 13²-hydroxybacteriochlorophyll a [BChl-13²-OH]BChl-13²-OH [compound 7b], a compound of formula I wherein $R_1$ is phytyl, $R_2$ is COOCH$_3$, $R_3$ is OH, R4 at position 3 is acetyl and at position 8 is ethyl, was prepared by hydroxylation of Bchl [7a] at position C-13² by storage of 7a in methanol for 5–7 days in the dark at 4° C. (Struck and Scheer, 1990). Alternatively, the LiBr-procedure according to Schaber et al., 1984, was used, which resulted in less by-products. Purification was done in each case on preparative (20×20 cm²) silica-gel plates (Silica gel 60 H, Merck) or columns with toluene/acetone (9:1, v:v) as eluent. The greenish-blue band containing the title product ($R_f$~0.4) was mechanically detached and unreacted Bchl a was extracted from SiO$_2$ with acetone.

(iii) Demetalation of BChl and BChl-13²-OH. BPhe [compound 1a] and BPhe-13²-OH [compound 1b] were obtained by demetalation of BChl [7a] and BChl-13²-OH [7b], respectively, according to Rosenbach-Belkin, 1988, with a small amount of acetic acid (the pigment is just dissolved). After demetalation, which occurs immediately, the acetic acid was removed by a stream of N$_2$, and the BPhe and BPhe-13²-OH were recovered as solid products.

(iv) Chlorophyllase (Chlase). Chlase acetone powder was prepared from *Melia azedarach* L. China tree leaves as described in EP 0584552.

(v) Cell Culture. The M2R mouse melanoma cells are cultured as monolayers in Dulbecco's modified Eagle's medium/F12 containing 25 mM HEPES pH 7.4, 10% fetal bovine serum, glutamine 2 mM, penicillin 0.06 mg/ml and streptomycin 0.1 mg/ml at 37° C. in a humidified atmosphere of 8% CO$_2$ as previously described (Gerst et al., 1986).

(vi) Cell photocytotoxicity studies. The M2R mouse melanoma cells (1×10⁵ cells/well) are cultured in 24 well microplates and grown for 24 h to about 2×10⁵ cells/well, approximately 70–80% confluency. The [M]—Bchl derivative is dissolved in culture medium and dispersed by sonication. Photosan-3 (commercially available HPD) is diluted to its final concentration in culture medium. The medium is replaced with serum-free medium and cells are incubated in the dark with the desired concentration of photosensitizers. Following 2 h of incubation the cells are irradiated at room temperature for 5 min from the bottom of the plate. The medium is replaced by serum containing medium and the culture plates are placed back in the incubator for 24 h. Cytotoxic efficiency in the cell culture is determined by (i) microscopic examination of cell morphology, (ii) fluorescence microscopy of cells following treatment with vital stain (propidium iodide [PID][2,7-diamino-9-phenyl-10-(diethylaminopropyl)-phenathridinium iodide methiodide]), which selectively accumulates in nuclei of damaged cells, and (iii) [³H]thymidine incorporation as further described below. Control experiments include (1) untreated cells kept in the dark, (2) untreated cells illuminated, and (3) cells treated with the drug but kept in the dark.

(vii) Light source. The light source for irradiation is a home-built 250 W halogen lamp focused through a 10 cm water filter on a glass support and fitted with a liquid filter (chlorophyll a O.D.=10.00 at 660 nm). The light dose is adjusted to 45 m W/cm² in all cases.

(viii) [³H]thymidine incorporation. Twenty four hours after PDT, cell cultures are pulsed with 1 $\mu$Ci/ml [³H] thymidine for 2 h at 37° C. Cultures are then washed twice with phosphate-buffered saline, treated with 7.5% cold trichloroacetic acid for 30 min at 4° C. and washed twice with ethanol. Sodium hydroxide (1 N, 300 $\mu$l/well) is added and the plates were kept for 10 min at 37° C. Samples of 100 $\mu$l are transferred to scintillation vials, neutralized with 100 $\mu$l 1 N HCl and radioactivity was counted by liquid scintillation counting in 4 mL (20:8 [vol/vol]) xylene scintillator lumax mixture according to Chen et al., 1988.

Example 1

Preparation of [Zn]—BChl and [Zn]—BChl-13²-OH by Direct Metalation

[Zn]—BChl [compound 6a] and [Zn]—BChl-13²-OH [compound 6b] were prepared by direct metalation of BPhe [1a} and BPhe-13²-OH [1b], respectively, by the acetate-lacetic acid or acetate/dimethylfortnamide method.

1a. Acetate/dimethylformamide (DhM Method

[Zn]—BChl and [Zn]—BChl-13²-OH [6a, 6b] were prepared by refluxing BPhe and BPhe-13²-OH (1a, 1b), respectively, (~70 $\mu$M) in DMF with a 1000-fold excess of anhydrous Zn(OAc)$_2$ for 60 (75) minutes at 110° C. (reflux at 163° C. decreses the reaction time to 5 minutes). The reaction was followed spectroscopically and ran to completion. Isolation and purification of products was done as for the Cd complexes 8a, 8b hereinafter (yield: 80%).

1b Acetate/Acetic Acid Method.

[Zn]—BChl and [Zn]—²-BChl-13²-OH (6a,6b) were prepared by refluxing 1a,1b or 7a,7b, (~70 $\mu$M) in glacial acetic acid, with a 250-fold excess of anhydrous Zn(OAc)$_2$ and sodium ascorbate 50 mM for 120 (30) minutes at 100° C. The acetic acid was then evaporated in a stream of N$_2$, the Zn complex extracted with diethyl ether and purified on a preparative ModCol HPLC column (250×25.4 mm) packed with Bakerbond Silica NP (particle size 10 $\mu$m; pore diameter 150). Compound 6a was eluted isocratically (10 mil/min) of 2-propanol (5%), methanol (5%) and n-hexane (90%, v/v) with a retention time of about 17 min, with ~75% yield of the purified compound. Compound 6b was purified by column chromatography on silica gel, using the same solvent mixture as for HPLC, giving a yield of 90–95%.

Example 2

Preparation of [Zn]—BChl-3-vinyl and [Zn]—BCbl-3-vinyl-13²-OH by Direct Metalation Metalation by the acetate/DMF method as in Example 1a above can be extended to other derivatives of BPhe, when reaction conditions are slightly varied. For instance, metalation of 3-vinyl-BPhe or 3-vinyl-i3²-hydroxy-BPhe with Zn(OAc)$_2$ proceeds under identical conditions within ~40 minutes at 120° C.

Example 3

Preparation of [Zn]—BChl-13²-Decarbometboxy by Direct Metalation

The Zn-complexes of 13²-decarbomethoxy-BPhe (or 13²-decarbomethoxy-BChl) are obtained under the same condi-

Example 4

Preparation of [Cu]-BChl, [Cu]-BChl-13²-OH and [Cu]-BChl-13²-Decarbomethoxy by Direct Metalation

[Cu]-BChl (5a) was prepared by refluxing 1a or 7a, (~70 μM) in glacial acetic acid, with a 250-fold excess of anhydrous $Cu_2O$ and sodium ascorbate (50 M) for 15 minutes at 100° C. [Cu]—BCb]-13²-OH (5b) was formed at ambient temperature by mixing 1b or 7b, (~70 μM) in glacial acetic acid, with a 250-fold excess of anhydrous $Cu_2O$ and sodium ascorbate 50 mM. The Cu-derivatives of 13²-decarbomethoxy-BPhe (or 13²-decarbomethoxy-BChl) was obtained at identical conditions as described for 5b. In spite of using $Cu_2O$, the Cu complexes were formed in all cases due to the presence of residual oxygen or disproportionation. Isolation and purification was done as described in Example 1b above for the Zn complexes prepared by the glacial acetic acid method, yielding ~75% (5a), ~90% (5b) and 90% (Cu-derivative of 13²-decarbomethoxy-BChl), respectively.

Example 5

Preparation of [Cd]—BChl by direct metalation of BPbe

[Cd]—BChl was prepared by refluxing about 70 μM BPhe in dimethylformamide with a 300-fold excess of anhydrous $Cd(OAc)_2$ for 40 min. at 130° C. The reaction was followed spectroscopically and run to completion. The crude products isolated by partitioning between diethyl ether (DE) and $NaHCO_3$-saturated water can be purified on silica gel under reducing conditions (15% sodium ascorbate admixed) with toluene/acetone/triethylamine (88/10/2 v/v/v) as eluent. The reaction and work-up, are carried out under strict Ar protection. The blue band of pure [Cd]—BChl ($R_f$~0.7) is mechanically detached and extracted with diethyl ether/water as described above for the crude product. The pure product was used in all transmetalation procedures described below. Its spectral properties (compound 8a) are presented in Table 1.

Example 6

Preparation of [M]-BChl and [M]—BChl-13²-OH complexes of Pd. Co. Ni. Cu, Zn, Cd and Mn by transmetalation of [Cd]—BChl and [Cd]—BCbl-13²-OH For the preparation of the [Pd]-BChl derivative (2a), [Cd]—BChl (8a) from Example 5 was dissolved in dry acetone (A770=5 cm$^{-1}$, ~50 μM) under strict Ar protection to prevent from uncontrolled oxidation at the positions C-7 and C-8. After about 15 min. $PdCl_2$ (Merck, p.a.) was added (~30 mg/100 ml solution) and the reaction mixture was refluxed for 40 min. The reaction can be followed spectroscopically (Qx-band shifts from ~590 nm to ~530 nm upon product formation). The essentially pure product was isolated by extraction with diethyl ether/water as described in Example 5 for [Cd]—BChl. If necessary, further purification is carried out on silica-gel plates as described for [Cd]—BChl. The spectral properties of Pd-BChl (2a) are characterized in Table 1.

In a similar way, [Pd]—BChl-13²-OH (2b) was prepared by transmetalation of [Cd]—BChl-13²-OH and the metal complexes of Co, Ni, Cu, Zn and Mn of Bchl (compounds 3a, 4a, 5a, 6a 9a) and of BChl-13²-OH (compounds 3b, 4b, 5b, 6b 9b) were prepared by reaction of [Cd]—BChl and BChl-13²-OH, respectively, with the corresponding metal chlorides. The anhydrous metal chlorides were added at a 10-fold molar excess (Cu: 5a, 5b; Zn: 6a,6b), 100-fold molar excess (Co: 3a,3b), or to saturation as Pd (Ni: 3a,3b; Mn: 9a,9b). The reactions occurred practically instantaneously at 25° C., except for Pd and Ni (about 30–40 min reflux), and were followed spectroscopically. Small amounts of C7-C8 oxidized products ($\lambda_{max}$~680 nm) were formed due to the presence of residual oxygen and can be suppressed by addition of sodium ascorbate (saturated). Isolation and purification of products was done as for [Cd]—BChl in Example 5 above. The products were characterized by absorption, fluorescence, $^1$H-NMR and FAB-MS as shown in Table 1. UV/VIS absorption spectra were recorded on a Perkin Elmer Lamnda 2 spectrophotometer, fluorescence emissions intensity on a Spex Fluorolog 221 equipped with a 450W Xwnon-lamp and normalized to the sensitivity of the photomultiplier tube and excitation energy. Maximum optical densities for fluorescence measurements were <0.1cm$^{-1}$ and excitation was into the $Q_x$-absorption band of 1a,1b to 9a,9b. Circular dichroism spectra (CD) were recorded on a Dichrograph CD6 (Jobin Yvon). FAB-MS were recorded on a CH7a/SS mas spectrometer-(Varian MAT) or a Finigan MAT 9000 with a Cs-gun where liquid-surface ionisation was done in a matrix of m-hydroxy-benzyl alcohol. $^1$H-NMR spectra were recorded on a 360 MHz-Bruker model AM360. Standard solvent was pyridine-$d_5$, chemical shifts are in ppm against tetramethylsilane as internal standard. Extinction coefficients were determined by ICP/ICPMS-atom absorption spectra (AAS) of the central metals; before combustion, the solvent in samples of 1a,1b to 9a,9b with quantified optical densities, was first evaporated in quartz glass tubes and the samples then treated with concentrated nitric acid to allow complete release of the metal.

TABLE 1

Spectral Properties of 1a, 1b—9a, 9b[a]

| compound | Absorption[b] $\lambda_{max}$[nm](ϵ[10$^{-3}$ M$^{-1}$ cm$^{-1}$]) | | | | Emission[c] | | FAB—MS |
|---|---|---|---|---|---|---|---|
| Ion | $B_Y$ | $B_X$ | $Q_X$ | $Q_Y$ | $\lambda_{max}$[nm] | $\chi_M/r_i^d$ | Molecular |
| 1a(+)[e] | 356 (113) | 383 (62.7) | 525 (28.3) | 750 (67.5) | 759 | | |
|  | 362 (92.3) | 389 (49.3) | 532 (26.2) | 754 (56.4) | | | |
| 2a(+) | 331 (18.1) | 383 (15.4) | 529 (6.0) | 753 (38.1) | 764 (755) | [3.44] | 992 ($^{106}$Pd) |

TABLE 1-continued

Spectral Properties of 1a, 1b—9a, 9b[a]

| compound | Absorption[b] $\lambda_{max}$[nm]($\epsilon$[$10^{-3}$ $M^{-1}$ $cm^{-1}$]) | | | | Emission[c] $\lambda_{max}$[nm] | $\chi_M/r_i^d$ | FAB—MS Molecular |
|---|---|---|---|---|---|---|---|
| Ion | $B_Y$ | $B_X$ | $Q_X$ | $Q_Y$ | | | |
| 3a(−) | 334 (14.0) 336 (34.8) | 388 (11.5) 388 (27.1) | 535 (5.6) 531 (8.9) | 763 (25.5) 766 (63.7) | —[f] | [3.21][g] | 945 ($^{59}$Co) |
| 4a(−)[h] | 355 (40.6) 335 (45.7) | 386 (27.5) 390 (30.4) | 562 (10.2) 531 (11.4) | 767 (56.3) 779 (63.0) | —[f] | [3.18] | 944 ($^{59}$Ni) |
| 5a(−) | 366 (49.2) 342 (53.3) | 391 (30.3) 390 (42.9) | 598 (16.1) 538 (14.5) | 771 (71.8) 771 (64.1) | —[f] | 2.86 [3.06] | 949 ($^{63}$Cu) |
| 6a(+) | 358 (44.7) 353 (58.9) | 395 (31.9) 389 (39.7) | 573 (12.2) 558 (18.0) | 780 (56.1) 762 (67.7) | 782 (772) | [2.48] | 950 ($^{64}$Zn) |
| 7(+) | 364 (52.4) 357 (73.3) 374 (57.7) | 390 (31.7) 390 (48.0) not resolved | 579 (16.5) 573 (20.8) 612 (16.9) | 773 (57.1) 771 (91.0) 781 (76.0) | 788 (778) | 1.82 | 910 ($^{24}$Mg) |
| 8a(+) | 359 (80.3) 386 (65.6) | 389 (53.5) 391 (44.1) | 575 (22.3) 593 (19.4) | 761 (88.3) 773 (69.6) | 778 (774) | 1.78 | 1000 ($^{114}$Cd) |
| 9a(−) | 362 (71.8) 373 (64.4) | 392 (43.0) not resolved | 587 (18.0) 601 (16.4) | 770 (76.7) 780 (66.0) | —[f] | 1.89 | 941 ($^{55}$Mn) |

Example 7

Transesterification of [Pd]—BChl and Peripherally-modified BChls to the $17^3$-ethyl Ester For the preparation of Pd-Bacteriopheophorbide a ethylester, [Pd]—BChl was dissolved in chloroform (1 mg/ml) and an identical volume of ethanol containing 5% $H_2SO_4$ v/v was added. The mixture was refluxed in an Ar-atmosphere for 90 min. Then the [Pd]—BPhe (100 mg) was transesterified in 50 ml sulfuric acid in ethanol/chloroform (1:1/v:v) by refluxing under Ar for 2.5 hours. Then the reaction mixture was diluted with ether, washed several times with 10% aqueous sodium bicarbonate solution. Subsequently, the organic phase was dried and evaporated. By preparative TLC under nitrogen on silica gel, eluting, with 8% acetone in toluene, the slower moving of the two bands obtained is the title compound ($R_f$0.75). VIS in either: $\lambda_{max}$[nm] (relative intensity) 329 (0.45); 385 (0.39); 527 (0.13); 755 (0.1). $^1$H-NMR [ppm]: 9.25, 8.80, 8.70 (each s, 1H, 5-, 10-, 20-H); 4.55 (q, 1H, 18-H); 4.45 (d, 1H, 17-H); 4.10 (q, 2H, 8-$CH_2CH_3$); 3.85 (s, $13^2$-$CO_2CH_3$); 3.7 (d. 1H, 7-H); 3.6 (q, 3H, $17^3$-$CH_2CH_3$); 3.50, 3.32 (each s, 1H, 12-$CH_3$); 3.30 (m, 1H, 8-H); 3.06 (s, 3H, 3-$COCH_3$); 3.04 (d, 3H, 7-$CH_3$); 2.45 (2H, $17^1$-$H_2$); 2.45 (2H, $17^2$-$H_2$) 1.75 (d, 3H, 18-$CH_3$); 1.65 (t, 3H, 8 $CH_2CH_3$); 1.38 (t, 3H, $17^3$-$CH_2CH_3$); 0.10 and −1,90 (s, 2H, 2 NH). FAB-MS calculated for Pd—$C_{37}H_{40}N_{40}N_4O_6$: 742.38 (M+1). Found 742.2 (M+1).

Ethyl and other esters of other acid-stable metal complexes, like Ni, Cu, Zn, of BChl derivatives can be prepared in a similar way.

Example 8

Preparation of [Pd]—BChl-$17^3$-seryl methyl ester [Pd]—BChl-$17^3$-L-Ser-OMe ([Pd]—BChl-Ser)

Enzymatic transesterification of [Pd]—BChl prepared in Example 6 above with L-serine methyl ester hydrochloride (Sigma) was carried out with chlorophyllase acetone powder as described in EP 0584552 producing the title compound, herein designated [Pd]—BChl-Ser, a compound of formula I' herein wherein $R'_1$ is the seryl methyl ester residue linked to the COO— group through the serine hydroxy group.

By the same enzymatic transesterification procedure, corresponding $17^3$-seryl methyl esters of other metal complexes [M]-Bchl according to the invention can be prepared as well as [M]-Bchl-$17^2$-esters with other serine derivatives, e.g. N-trityl-L-serine methyl ester and N-carbobenzoxyseryl serine methyl ester, or with tyrosine derivatives, e.g. N-tert-butoxycarbonyltyrosine methyl ester, as described in EP 0584552.

Example 9

Phototoxicity in Vitro of [Pd]—BChl-Ser

9a. Bacteria and Virus

The phototoxicity assay consists of three discrete steps: incubation of a bacterial solution with the sensitizer, illumination and assessment of phototoxicity.

Suspensions (~$1\times10^7$ bacteria/200 µl) of fresh *S. aureus* in phosphate-buffered saline (PBS) were incubated with the given concentrations of the sensitizers [Pd]—BChl-Ser or BChl-Ser for 1 hour in the dark and subsequently washed free of the pigment by centrifugation and resuspension in PBS. The washed bacterial suspensions were illuminated for 5 min using as light source a self-built Xenon lamp with vertical emission of 1000 lux/$cm^2$ at the target level, using a liquid filter (chlorophyll a O. D.=10.00 at 660 nm). The photodynamic damage was assessed by determination of bacterial. survival: samples of the irradiated bacterial suspension (30 µl) were cultured in 3 ml of brain heart infusion (BHI) liquid bacterial culture medium for 2 h at 37° C. under shaking. Bacterial density was measured by turbidity at $\lambda$=660 mn.

Each experiment consisted of (a) one experimental (bacteria submitted to the complete treatment) and three control groups: (b) bacteria irradiated without sensitizer, (c) unirradiated bacteria treated with sensitizer, and (d) untreated bacteria (100% of survival).

As shown in FIG. 1, the phototoxic effects of [Pd]—BChl-Ser are dose dependent with respect to sensitizer concentrations ($LD_{50}$~0.6 µM) and no toxicity was conferred in the dark. Similar results were obtained with BChl-Ser, tested as comparison under the same conditions, with a slightly but insignificantly lower $LD_{50}$.

The assay was repeated with *B. subtilis* and *Propionibacterium acnes* and with Herpes Simplex Virus 1 (HSV-1) both in suspension and in infected cells, and similar results of phototoxicity were obtained (not shown).

9b. Melanoma Cells

The assay was conducted as described in Materials and Methods hereinabove, sections (iv) to (viii). Monolayers of M2R cells were incubated with the indicated concentrations of [Pd]—BChl-Ser for 1 h and subjected to photodynamic treatment as described above. Photocytotoxicity was assessed by [$^3$H] thymidine incorporation and percent survival of the treated cells and appropriate controls are described in FIG. 2. Survival of untreated cells was taken as 100%.

Figure 2:
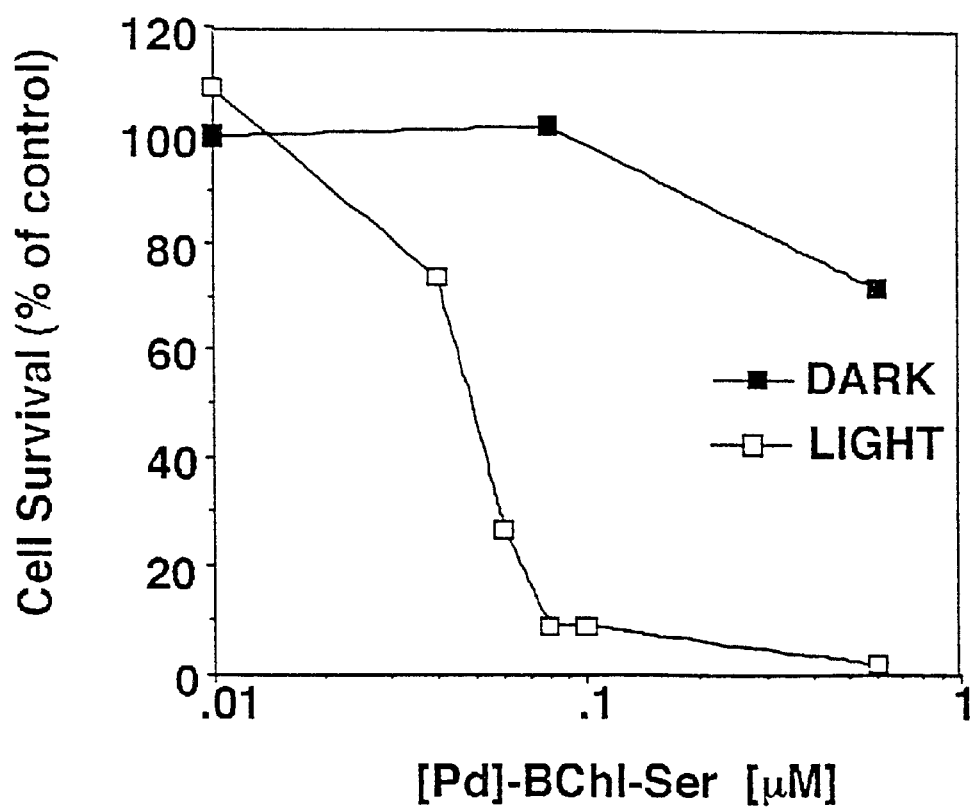
FIG. 2 shows the phototoxicity of [Pd]—BChl-Ser on M2R melanoma cells in culture by [$^3$H]thymidine incorporation.

It can be seen in FIG. 2 that the phototoxic effect was dose dependent with respect to [Pd]—BChl-Ser concentration with an approximate $LD_{50}$ of 0.05 µM. The phototoxic effect was not seen in the dark controls.

REFERENCES

1. Buchler, J. W., 1975, "Static coordination chemistry of metalloporphyrins", in *Porphyrins and Metalloporphyrins*, Smith, K. M., ed., pp 157–232, Elsevier, N.Y.
2. Chen, L., Y. Mory, A. Zilberstein and M. Revel, 1988, Proc. Natl. Acad. Sci. USA, vol. 85, pp. 8037–41.
3. DeJordy, J. O., P. Bendel, A. Horowitz, Y. Salomon and H. Degani, 1992, J. Magn. reson. Imag., vol. 2, pp. 695–700.
4. Gerst, J. E., J. Sole, J. P. Mather and Y. Salomon, 1986, Mol. Cell. Endocrinal., vol. 46, pp. 137–47.
5. Hynninen P. H., in: Scheer, 1991, pp 145–209.
6. Losev et al., 1990, Opt. Spektrosk., vol. 69, pp. 97–101.
7. Matthews, J. L. et al., 1988,Transfusion, pp. 81–83.
8. Ofnata, T. and N. Murata, 1983, "Preparation of Chlorophyll a, Chlorophyll b and Bacteriochlorophyll a by column chromatography with DEAE-Sepharose Cl-6B and Sepharose Cl-6B", Plant Cell Physiol., vol. 24, pp. 1093–1100.
9. Rosenbach-Belkin, V., 1988, "The primary reactants in bacterial photosynthesis modelling by in vitro preparation", Ph. D. Thesis, Weizrnann Institute of Science, Israel.
10. Schaber, P. M., J. E. Hunt, R. Fries and J. J. Katz, 1984,. J. Chromatogr. 316, 25–41.
11. Scheer, H., ed., 1991, *Chlorophylls*, CRC Press, Boca Raton, Florida.
12. Scherz, A. and W. W. Parson, 1984, Biochim. Biophys. Acta, vol. 766, pp. 653–55.
13. Strell, M. and Urumow, T.,1977, Liebigs Ann. Chem., pp. 970–974.
14. Struck, A., 1990, "Chemisch modifizierte Bakteriochlorophylle und-phaeophytine in den Bindungsstellen $B_{A,B}$ und $H_{A,B}$ von photosynthetischen Reaktionszentren aus Rhodobacter sphaeroides R26: Pigmentsynthese, Pigmentaustausch und Spektroskopie", Ph. D. Thesis, University of Munich, Germany.
15. Struck, A. et al., 1992, Bacteriochlorophylls modified at position C-3: Long-range intramolecular interaction with position C-13.2, Biochim. Biophys. Acta, 1 101:321–328.
16. Struck, A. and Scheer, H., 1990, "Modified reaction centers from *Rhodobactersphaeroides* R26. Exchange of monomeric bacteriochlorophyll with $13^2$-hydroxy-bacteriochlorophyll", FEBS Lett. 261, pp. 385–388
17. Svec, W. A., 1991, "The distribution and extraction of the Chlorophylls", in:Scheer, 1991, pp. 89–102.
18. Wasielewsky, M. R., 1977, "A mild method for the introduction of Magnesium into bacteriopheophytin-a", Tetrahedron Letters, pp. 1373–76.

What is claimed is:

1. A metalated bacteriochlorophyll of the formula I', II' or III':

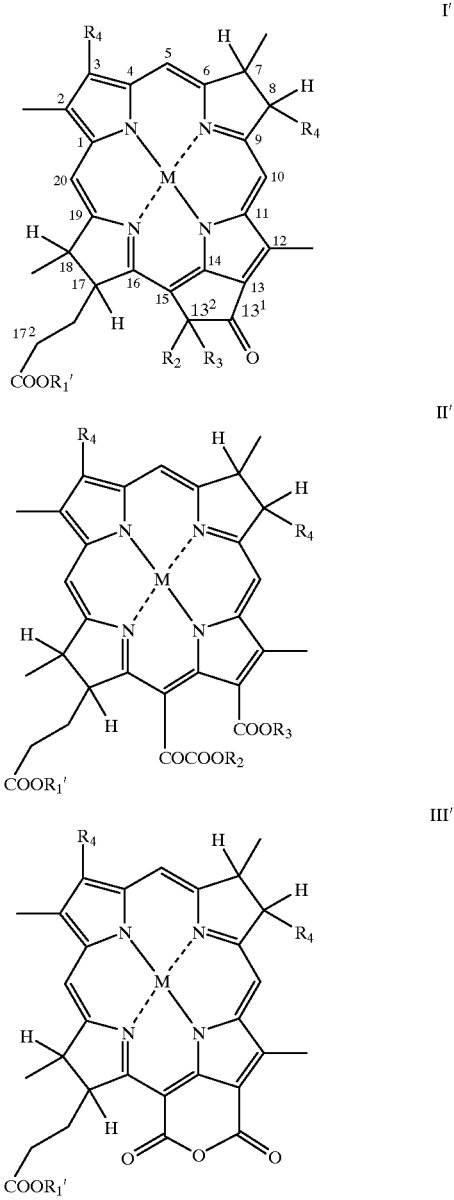

wherein $R'_1$ is selected from the group consisting of:

(a) a $C_1$–$C_{25}$ hydrocarbyl moiety optionally substituted by halogen, OH, oxo, CHO, COOH, or $NH_2$, or such a moiety interrupted by one or more heteroatoms selected from O, S and NH, or by a phenyl ring;

(b) an amino acid or a peptide containing a hydroxy group or a derivative thereof selected from the group consisting of esters and N-protected derivatives, wherein said hydroxylated amino acid or derivative thereof is linked to the COO— residue through the hydroxy group;

(c) a peptide as defined in (b) linked to the COO— residue via said $C_1$–$C_{25}$, hydrocarbyl moiety optionally substituted by halogen, OH, oxo, CHO, COOH, or $NH_2$, or such moiety interrupted by one or more heteroatoms selected from O, S and NH, or by a phenyl ring, and further substituted by an end group selected from OH, COOH, or $NH_2$; and (d) a cell-specific ligand selected from the group consisting of a peptide and a protein directly linked to the COO— moiety or via said $C_1$–$C_{25}$ hydrocarbyl moiety optionally substituted by halogen, OH, oxo, CHO, COOH, or $NH_2$, or interrupted by one or more heteroatoms selected from O, S and NH, or by a phenyl ring, and fur ther substituted by an end group selected from OH, COOH, or $NH_2$;

$R_2$ is H, OH or $COOR_5$, wherein $R_5$ is $C_1$–$C_{12}$ alkyl or $C_3$–$C_{12}$ cycloalkyl;

$R_3$ is H, OH or $C_1$–$C_{12}$ alkyl or alkoxy;

$R_4$ is each independently selected from the group consisting of vinyl, ethyl, acetyl, 1-hydroxyethyl and ethers and esters thereof; and M represents a metal with an ionic radius smaller than that of Cd (r≅95), said metal M being selected from the group consisting of a divalent metal selected from the group consisting of Pd, Co, Ni and Mn, a trivalent metal selected from the group consisting of Fe, Mn and Cr, and a tetravalent metal selected from the group consisting of Sn and Pt;

but excluding the compounds of formula I' wherein $R_2$ is $COOCH_3$, $R_3$ is H, $R_4$ at position 3 is acetyl and at position 8 is ethyl, $R'_1$ is phytyl or ethyl and M is Pd.

2. A metalated bacteriochlorophyll derivative according to claim 1 of formula I' wherein $R'_1$ is phytyl or geranylgeranyl, $R_2$ is $COOCH_3$, $R_3$ is H, $R_4$ at position 3 is acetyl and at position 8 is ethyl, and M is Co, Ni, Zn, Cd or Mn.

3. A metalated bacteriochlorophyll according to claim 1 of formula I' wherein $R'_1$ is phytyl or geranylgeranyl, $R_2$ is $COOCH_3$, $R_3$ is OH, $R_4$ at position 3 is acetyl and at position 8 is ethyl, and M is Pd, Co, Ni, Cd or Mn.

4. A metalated bacteriochlorophyll according to claim 1 of formula I' wherein $R'_1$ is ethyl, $R_2$ is $COOCH_3$, $R_3$ is H, $R_4$ at position 3 is acetyl and at position 8 is ethyl, and M is Ni.

5. A metalated bacteriochlorophyll according to claim 1 of formula I' wherein $R'_1$ is seryl methyl ester, $R_2$ is $COOCH_3$, $R_3$ is H, $R_4$ at position 3 is acetyl and at position 8 is ethyl, and M is Pd.

6. A pharmaceutical composition comprising a metalated bacteriochlorophyll of formula I', II' or III' as defined in claim 1 and a pharmaceutically acceptable carrier.

7. A pharmaceutical composition according to claim 6 wherein the metalated bacteriochlorophyll is a compound of said formula I' wherein $R'_1$ is seryl methyl ester, $R_2$ is $COOCH_3$, $R_3$ is H, $R_4$ at position 3 is acetyl and at position 8 is ethyl, and M is Pd.

8. In a method for photodynamic therapy using a photosensitizer, the improvement wherein said photosensitizer is a metalated bacteriochlorophyll of formula I', II', or III' as defined in claim 1.

9. In a method for the diagnosis of tumors using a photosensitizer, the improvement wherein said photosensitizer is a metalated bacteriochlorophyll of formula I', II', or III' as defined in claim 1.

10. In a method for killing cells or infectious agents comprising bacteria and viruses, using a photosensitizer, the improvement wherein said photosensitizer is a metalated bacteriochlorophyll of formula I', II', or III' as defined in claim 1.

11. A method in accordance with claim 10, for killing of infectious agents in biological products.

12. A process for the preparation of a synthetic metalated bacteriochlorophyll of the formula:

[M]—BChl wherein

BChl represents a demetalated natural or synthetic bacteriochlorophyll carrying at position $17^3$ a group —$COOR_1$ wherein $R_1$ is a $C_1$–$C_{25}$ hydrocarbyl moiety, and M represents a metal with an ionic radius smaller than that of Cd (r 95), said metal M being selected from the group consisting of a divalent metal selected from the group consisting of Pd, Co, Ni, Cu, Zn and Mn, a trivalent metal selected from the group consisting of Fe, Mn and Cr, and a tetravalent metal selected from the group consisting of Sn and Pt, which process comprises:

(i) reacting a bacteriopheophytin, dissolved in dimethyl formamide, with dehydrated Cd acetate in argon atmosphere, and recovering the [Cd]—BChl complex from the reaction mixture by chromatography under reducing conditions;

(ii) reacting the [Cd]—BChl complex produced in step (i), dissolved in dry acetone, with an appropriate dehydrated metal M salt selected from metal M chloride, acetate and acetylacetonate in argon atmosphere; and (iii) recovering the metalated [M]—B—Chl from the reaction mixture.

13. A process according to claim 12 wherein said metal M salt employed in step (ii) is a metal chloride.

14. A process according to claim 12 wherein said steps (i) and (ii) are combined into one single step, and the bacteriopheophytin derivative is reacted with an excess of the appropriate dehydrated metal M salt in the presence of catalytic amounts of the dehydrated Cd acetate in dimethylformamide or acetone.

15. A process according to claim 12 wherein said bacteriopheophytin is selected from a compound or the formula I, II or III:

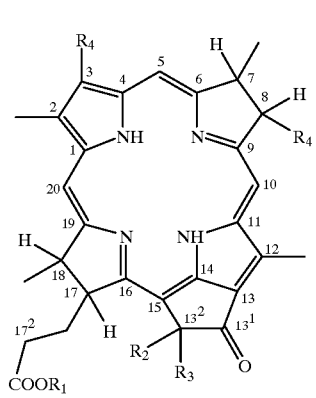

I

-continued

II

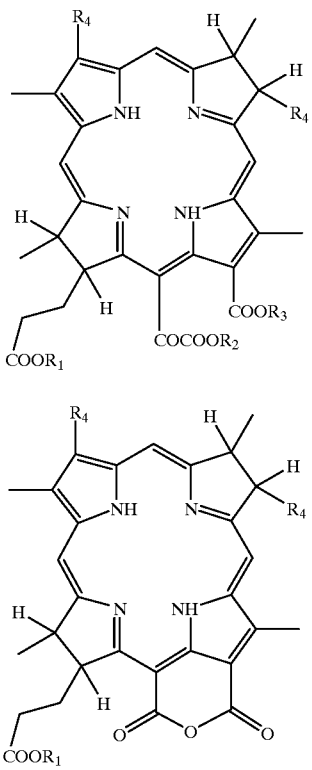

II'

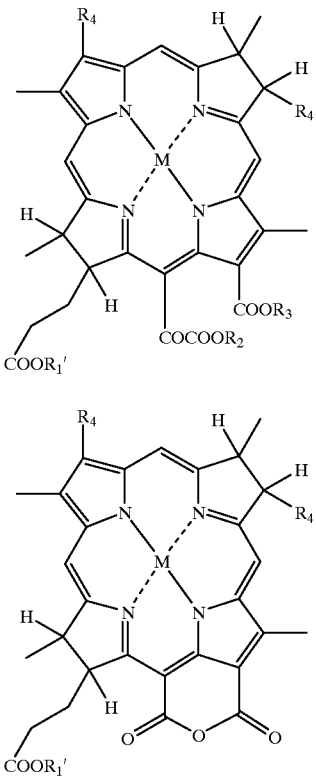

III

III' wherein $R_1$ is a $C_1$–$C_{25}$ hydrocarbyl moiety;

$R_2$ is H, OH or $COOR_5$, wherein $R_5$ is $C_1$–$C_{12}$ alkyl or $C_3$–$C_{12}$ cycloalkyl;

$R_3$ is H, OH or $C_1$–$C_{13}$ alkyl or alkoxy; and $R_4$ is each independently selected from the group consisting of vinyl, ethyl, acetyl, 1-hydroxyethyl and ethers and esters thereof.

16. A process according to claim 15, wherein the [M]—BChl recovered in step (iii) is further subjected to transesterification at position $17^3$, thus producing [M]—BChl of the formula I', II' or III':

I'

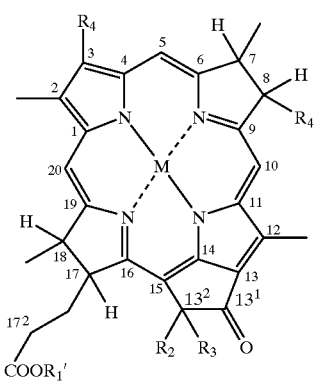

wherein $R'_1$ is selected from the group consisting of:
(a) a $C_1$–$C_{25}$ hydrocarbyl moiety optionally substituted by halogen, OH, oxo, CHO, COOH, or $NH_2$, or such a moiety interrupted by one or more heteroatoms selected from O, S and NH, or by a phenyl ring;
(b) an amino acid or a peptide containing a hydroxy group or a derivative thereof selected from the group consisting of esters and N-protected derivatives, wherein said hydroxylated amino acid or derivative thereof is linked to the COO— residue through the hydroxy group;
(c) a peptide as defined in (b) linked to the COO— residue via said $C_1$–$C_{25}$ hydrocarbyl moiety optionally substituted by halogen, OH, oxo, CHO, COO, or $NH_2$, or such moiety interrupted by one or more heteroatoms selected from O, S and NH, or by a phenyl ring, and further substituted by an end group selected from OH, COOH, or $NH_2$; and
(d) a cell-specific ligand selected from the group consisting of a peptide and a protein directly linked to the COO— moiety or via said $C_1$–$C_{25}$ hydrocarbyl moiety optionally substituted by halogen, OH, oxo, CHO, COOH, or $NH_2$, or interrupted by one or more heteroatoms selected from O, S and NH, or by a phenyl ring, and further substituted by an end group selected from OH, COOH, or $NH_2$;

$R_2$ is H, OH or $COOR_5$, wherein $R_5$ is $C_1$–$C_{12}$ alkyl or $C_3$–$C_{12}$ cycloalkyl;

$R_3$ is H, OH or $C_1$–$C_{12}$ alkyl or alkoxy;

$R_4$ is each independently selected from the group consisting of vinyl, ethyl, acetyl, 1-hydroxyethyl and ethers and esters thereof; and M represents a metal with an ionic radius smaller than that of Cd (r≅95), said metal M being selected from the group consisting of a divalent metal selected from the group consisting of Pd, Co, Ni, Cu, Zn and Mn, a trivalent metal selected from the group consisting of Fe, Mn and Cr, and a tetravalent metal selected from the group consisting of Sn and Pt, which transesterification process comprises:

reacting said metalated [M]—BChl with a compound of the formula $R'_1$—OH, to obtain said compound of formula I', II' or III' wherein $R'_1$ is as defined above.

17. A process according to claim 15, wherein said bacteriopheophytin is a compound of the formula I wherein $R_1$ is phytyl or geronylgeronyl, $R_2$ is $COOCH_3$, $R_3$ is H or OH, and $R_4$ at position 3 is acetyl and at position 8 is ethyl, and wherein said metal M salt is a salt in which M is Pd, Cu, Ni, Co, Zn or Mn.

\* \* \* \* \*

UNITED STATES PATENT AND TRADEMARK OFFICE
CERTIFICATE OF CORRECTION

PATENT NO. : 6,333,319 B1
DATED : December 25, 2001
INVENTOR(S) : Avigdor Scherz et al.

It is certified that error appears in the above-identified patent and that said Letters Patent is hereby corrected as shown below:

Title page,
Item [56], References Cited, OTHER PUBLICATIONS,
"Strell et al," reference, delete "Meals" and insert therefor -- Metals --.
"Tamiaki et al," reference, delete "Bacgteriochlorin" and insert therefor -- Bacteriochlorin --.

Column 1,
Line 14, delete "teriochirophyll" and insert therefore -- teriochlorophyll --.
Line 33, delete "phytyl." and insert therefor -- phytyl, --.

Column 3,
Line 38, delete "Mn" and insert therefor -- $MN^{++}$ --.

Column 5,
Line 45, delete "$R'_1$" and insert therefor -- $R_1$ --.
Line 47, delete ": COOR5, wherein R5" and insert therefor -- $COOR_5$, wherein $R_5$ --.
Line 62, delete "[MN]" and insert therefor -- [M] --.

Column 6,
Line 56, delete "R'," and insert therefor -- $R_1$ --.

Column 7,
Line 55, after "step", delete ";".

Column 8,
Line 31, delete "educts" and insert therefor -- adducts --.
Line 32, delete "$CdCI_2$" and insert therefor -- $CdCl_2$ --.

Column 9,
Line 47, delete "eryymatic" and insert therefor -- enzymatic --.

Column 10,
Line 16, delete "Publishin" and insert therefor -- Publishing --.
Line 47, after "cells", delete the period and insert therefor a comma.

Column 11,
Line 11, delete "BChL" and insert therefor -- BChl. --.
Line 18, delete "OH]BChl" and insert therefor -- OH]. BChl --.

UNITED STATES PATENT AND TRADEMARK OFFICE
CERTIFICATE OF CORRECTION

PATENT NO.    : 6,333,319 B1
DATED         : December 25, 2001
INVENTOR(S)   : Avigdor Scherz et al.

It is certified that error appears in the above-identified patent and that said Letters Patent is hereby corrected as shown below:

Column 12,
Lines 26-27, delete "acetate-lac etic" and insert therefor -- acetate/acetic --.
Line 27, delete "dimethylfortnami de" and insert therefor -- dimethylformamide --.
Line 28, delete "DhM" and insert therefor -- DMF --.
Line 38, delete "[Zn]-$^2$-BChl" and insert therefor -- [Zn] -BChl --.
Line 54, delete "BCbl-3" and insert therefor -- BChl-3 --.
Line 59, delete "vinyl-i3$^2$" and insert therefor -- vinyl-13$^2$ --.

Column 13,
Line 13, delete "BCb]" and insert therefor -- BChl --.
Line 29, delete "BPbe" and insert therefor -- BPhe --.
Line 50, delete "Pd. Co. Ni. Cu. Zn. Cd" and insert therefor -- Pd, Co, Ni, Cu, Zn --.
Line 51, delete "BCbl" and insert therefor -- BChl --.

Column 14,
Line 34, delete "Lamnda" and insert therefor -- Lambda --.
Line 36, delete "Xwnon-lamp" and insert therefor -- Xenon-lamp --.
Line 42, delete "mas" and insert therefor -- mass --.

Column 15,
Before Example 7, please insert the following

--$^a$ The absorption and fluorescence spectra of the 13$^2$-OH pigments (1b-9b) were superimposable to those of the respective 13$^2$-H parent compounds, except for a systematic blue-shift of the $Q_X$ absorption (530-600 nm range) by ~ 5nm. The mass spectra were always shifted by 16 mass units to higher values. All wavelengths are in [nm]. $^b$ Absorption and extinction coefficients (by AAS) at 298 K in DE (upper line) and pyridine (lower line, *italics*). $^c$ Fluorescence in DE/petroleum ether/isopropanol (5:5:2; v/v/v) at 298K (77K). $^d$ Electronegativity ($\chi_M$) and effective ionic radii ($r_M$ in 10$^{-14}$m) for sixfold coordination (data in square brackets use radii for fourfold coordination) from Buchler, 1975. $^e$ $^1$H-NMR in pyridine-d$_5$; (+): sharp signals, (-): extensive line broadening due to paramagnetic central metal. $^f$ Not fluorescent (Spex fluorolog 221). $^h$ Sharp $^1$H-NMR signals in C$^2$H$_3$CN. --

Line 41, delete "R,$_f$0.75" and insert therefor -- R$_f$=0.75 --.

UNITED STATES PATENT AND TRADEMARK OFFICE
CERTIFICATE OF CORRECTION

PATENT NO. : 6,333,319 B1
DATED : December 25, 2001
INVENTOR(S) : Avigdor Scherz et al.

It is certified that error appears in the above-identified patent and that said Letters Patent is hereby corrected as shown below:

Column 16,
Line 50, delete the period after the first instance of "bacterial"

Column 17,
Line 40, delete "Weizrnann" and insert therefor -- Weizmann --.
Line 60, delete "*Rhodobactersphaeroides*" and insert therefor -- *Rhodobacter sphaeroides* --.
Line 60, after "R26.", insert -- 1. --.

Column 19,
Line 14, delete "fur ther" and insert therefor -- further --.
Line 35, delete ", Zn, Cd".
Line 39, delete ", Cd".

Column 20,
Line 18, delete "(r 95" and insert therefor -- (r$\cong$95) --.
Line 37, delete "[M]-B-Chl" and insert therefor -- [M]-BChl --.

Column 21,
Line 42, delete "$C_1$-$C_{13}$" and insert therefor -- $C_1$-$C_{12}$ --.

Column 24,
Line 3, delete "geronylgeronyl" and insert therefor -- geranylgeranyl --.

Signed and Sealed this

Twenty-fifth Day of January, 2005

JON W. DUDAS
*Director of the United States Patent and Trademark Office*